(12) United States Patent
Hendriks et al.

(10) Patent No.: US 10,525,094 B2
(45) Date of Patent: Jan. 7, 2020

(54) DERMATOLOGICAL COMPOSITION BASED ON ALGAE AND OLIVE LEAF EXTRACTS

(71) Applicant: MEDICAL BRANDS RESEARCH B.V., Amsterdam (NL)

(72) Inventors: Maikel Hendriks, Amsterdam (NL); Pieternella Anna Maria Bouter, Amsterdam (NL); Maarten Casparus Van Den Ende, Amsterdam (NL)

(73) Assignee: MEDICAL BRANDS RESEARCH B.V., Amsterdam (NL)

( * ) Notice: Subject to any disclaimer, the term of this patent is extended or adjusted under 35 U.S.C. 154(b) by 343 days.

(21) Appl. No.: 15/107,224

(22) PCT Filed: Dec. 23, 2013

(86) PCT No.: PCT/EP2013/077944
§ 371 (c)(1),
(2) Date: Jun. 22, 2016

(87) PCT Pub. No.: WO2015/096856
PCT Pub. Date: Jul. 2, 2015

(65) Prior Publication Data
US 2016/0331797 A1    Nov. 17, 2016

(51) Int. Cl.
| A61K 36/63 | (2006.01) |
| A61K 38/10 | (2006.01) |
| A61K 31/05 | (2006.01) |
| A61K 35/748 | (2015.01) |
| A61K 9/00 | (2006.01) |
| A61K 38/08 | (2019.01) |
| A61P 31/04 | (2006.01) |
| A61P 31/10 | (2006.01) |
| A61P 31/12 | (2006.01) |
| A61M 35/00 | (2006.01) |

(52) U.S. Cl.
CPC ............ *A61K 36/63* (2013.01); *A61K 9/0014* (2013.01); *A61K 31/05* (2013.01); *A61K 35/748* (2013.01); *A61K 38/08* (2013.01); *A61K 38/10* (2013.01); *A61P 31/04* (2018.01); *A61P 31/10* (2018.01); *A61P 31/12* (2018.01); *A61M 35/003* (2013.01)

(58) Field of Classification Search
None
See application file for complete search history.

(56) References Cited

U.S. PATENT DOCUMENTS 6,743,449 B2 * 6/2004 Pinnell .................. A61K 8/602
424/59
8,808,706 B2  8/2014 Duncan et al.

FOREIGN PATENT DOCUMENTS

| AU | 2005301101 | 5/2006 |
| CA | 2 701 378 | 10/2011 |
| CN | 101068917 | 12/2010 |
| EP | 1 582 512 | 10/2005 |
| EP | 2 462 991 | 6/2012 |
| FR | 2 563 109 | 10/1985 |
| MD | 670 | 8/2013 |
| WO | WO 01/76579 | 10/2001 |
| WO | WO 2009/074644 | 6/2009 |

OTHER PUBLICATIONS

International Search Report for PCT/EP2013/077944 dated Feb. 6, 2014, 5 pages.
International Preliminary Report for Patentability for PCT/EP2013/077944 dated Feb. 29, 2016, 14 pages.

\* cited by examiner

*Primary Examiner* — Russell G Fiebig
(74) *Attorney, Agent, or Firm* — Nixon & Vanderhye P.C.

(57) ABSTRACT

The invention provides a dermatological composition comprising materials of algae origin (e.g. *Arthrospira platensis*) and olive leaf origin, the composition at least comprising a polypeptide and hydroxytyrosol. The composition is for use in the treatment and/or prevention of a dermatological microbial infection, e.g. nail fungus, Athlete's foot, wound, chickenpox, acne. The invention also provides an applicator device comprising such composition. Further, the invention provides a method for preparing such dermatological composition. Especially, the composition at least comprises a polypeptide and hydroxytyrosol.

17 Claims, No Drawings

DERMATOLOGICAL COMPOSITION BASED ON ALGAE AND OLIVE LEAF EXTRACTS

This application is the U.S. national phase of International Application No. PCT/EP2013/077944 filed 23 Dec. 2013 which designated the U.S., the entire content of which is hereby incorporated by reference.

FIELD OF THE INVENTION

The invention relates to a dermatological composition. Further, the invention relates also to a method for preparing such composition. The invention also relates to an application comprising a dermatological composition.

BACKGROUND OF THE INVENTION

Compositions for treatment of fungal infections etc. or other dermatological illnesses are known in the art. US2013210770, for instance, describes compounds useful for treating fungal infections, more specifically topical treatment of onychomycosis and/or cutaneous fungal infections. US2013210770 describes compounds that are active against fungi and have properties that allow the compound, when placed in contact with a patient, to reach the particular part of the skin, nail, hair, claw or hoof infected by the fungus. These compounds are alleged to have physiochemical properties that facilitate penetration of the nail plate. For instance, this document describes a pharmaceutical formulation comprising: a) a pharmaceutically acceptable excipient which is alcohol; b) a compound which penetrates the nail plate and travels through the nail plate to a nail bed underlying said nail plate; c) an emollient which is a cyclic polydimethylsiloxane containing from about 3 to about 9 silicon atoms; and having an efficacy coefficient against *Trichophyton rubrum* or *Trichophyton mentagrophytes* above 10; wherein the compound is present in said pharmaceutical formulation in a concentration of from about 0.5% to about 15%; and wherein said pharmaceutical formulation is for ungual administration to a human suffering from onychomycosis mediated at least in part by said *Trichophyton rubrum* or *Trichophyton mentagrophytes*.

SUMMARY OF THE INVENTION

Various compositions are known for use in the treatment of dermatological illnesses like athlete's foot, nail fungus, chickenpox, acne, etc. Many of these have no or only a moderate effect and/or have undesired side effects. Further, many of those compositions include non-natural components, which may be less desired. Hence, it is an aspect of the invention to provide an alternative dermatological composition, which preferably further at least partly obviates one or more of these drawbacks.

In a first aspect, the invention provides a (dermatological) composition comprising materials of algae origin and olive leaf origin, the composition at least comprising a one or more of a polypeptide and hydroxytyrosol. It was surprisingly found that the combination of the material of algae origin (especially including amongst others beneficial polypeptides) and the material of olive leaf origin (especially including the hydroxytyrosol having beneficial properties) provides a synergistic effect and appeared to be effective against microorganisms, such as bacteria or fungi, that could not be (well) treated with an algae composition or an olive leaf composition alone.

Herein, the terms "material of algae origin", material of "olive leaf origin" especially indicates that an extract of an alga or an extract of an olive leaf, respectively, are comprised by the composition. Hence, especially the invention provides a dermatological composition based on algae and olive leaf extracts.

The phrase "material of algae origin" may refer to a material based on one or more different types of algae. The term "algae" may also refer to Cyanobacteria. As indicted below, the material of algae origin, especially the algae extract, may especially be a material of *Arthrospira platensis* origin, especially an *Arthrospira platensis* extract (or extract of *Arthrospira platensis*).

The olive leaf extract used herein especially comprises hydroxytyrosol, and further also especially fatty acids, which demonstrate unique skin barrier properties as well as antimicrobial effects. The phrase "material of olive leaf origin" may refer to a material based on leaves of one or more different types of olives. The term "olive leaf extract" especially refers to an extract of leaves of the *Olea Europaea* (see also below).

The skin is the most important protector to the human body. It protects it from multitudinous external pathogens. Sebaceous glands are located in the skin that secretes multiple lipids, called sebum. These epidermal lipids contribute to essential skin functions as the barrier function and the maintenance of healthy skin. Consequently, they contribute to aging and to the conditioning and defense of this organ. Epidermal lipids provide a barrier against the movement of water and against a microorganism invasion. Sometimes, the skin has a lack in its barrier function and requires some help. Fatty acids can help to bring back this barrier.

Fatty acids in olives, such as especially linoleic and oleic acids, may have the best skin barrier properties. Further, linoleic and oleic acids can create a physical layer to protect the skin. These fatty acids also appear to have wound closing abilities. It further appears that oleic acids induce a faster wound closure than linoleic acid. Hence, the herein described composition may especially also comprise linoleic acid and/or oleic acid, especially both. Besides the protective barrier properties of fatty acids, the olive-leaf based composition contains another active compound, the antioxidant and polyphenol hydroxytyrosol. Hydroxytyrosol appears to be more cytotoxic than oleuropein, thus more effective against bacteria and seems to be (substantially) free from toxicity against mammalian cells. Challenge tests (see also below) for the antibacterial action have shown that the extract inactivates amongst others *Staphylococcus aureus* bacteria and staphylococcal enterotoxin A.

The mode of action of olive leaf based extract appears to have a physical mode of action where it focuses on the unwanted bacteria and does not affect mammalian cells, such as human cells. Olive polyphenols clearly show that hydroxytyrosol penetrates the structurally different cell membranes of both gram-negative and gram-positive bacteria. Phenolic and antioxidant compounds may cause disruption of cell peptidoglycans or damage the bacterial cell membrane or both. Eventually, the bacteria will get inactivated and abandoned from the body. The olive leaf extract may have one or more of an anti-microbial, anti-viral and an anti-fungal function.

Especially, as indicated above, as source of olive leaves the olive leaves of *Olea Europaea* are applied. Though others might also be applied, very good results were obtained with the *Olea Europaea*. A high concentrated extract may be applied (see also below for the algae material).

The extract may e.g. be obtained by a method including treating olive leaf with an aqueous liquid, especially an aqueous liquid comprising an alcohol, and providing an olive leaf extract. The alcohol may especially comprise a C2-C8, especially a C2-C6 alcohol, even more especially ethanol. The extraction may be done at elevated temperature, such as in the range of 20-100° C., such as 40-100° C. Hence, in a further embodiment the invention provides said (dermatological) composition wherein the materials of olive leaf origin are especially obtainable by such method including treating olive leaf with an aqueous liquid, especially an aqueous liquid comprising an alcohol, and providing an olive leaf extract.

It further appears surprisingly advantageous when the oleuropein, which is available in the olive leaf (extract), is converted, especially by hydrolysis to hydroxytyrosol (3,4-dihydroxyphenylethanol or 3,4-dihydroxyphenyl ethanol). As known in the art, hydrolysis may be performed by using an acid or alkaline liquid. Here, especially an alkaline liquid (i.e. pH>7, especially >8) is applied. Whereas prior art applications in general focus at oleuropein and its alleged beneficial properties, it was surprisingly found that reducing the oleuropein content and increasing the hydroxytyrosol content led to substantially better treatment (and/or prevention) results (of especially the herein indicated illnesses). Hydrolysis may be done during extraction or in a process subsequent to extraction. Especially, the weight ratio of oleuropein to hydroxytyrosol is <1, even more especially <0.1 (in the (dermatological) composition). Hence, the extract may e.g. be obtained by a method including treating olive leaf with an aqueous liquid and hydrolyzing the oleuropein in the extract until a weight ratio of oleuropein to hydroxytyrosol of <1 (or even smaller) is obtained, especially unit the weight ratio is <0.1 or smaller.

Hence, in a further aspect, the invention also provides a method for preparing a (dermatological) composition comprising materials of olive leaf origin, the method comprising treating olive leaf with an aqueous liquid comprising an alcohol and providing an olive leaf extract, and optionally hydrolysis of the (olive leaf) extract (or more precisely hydrolysis of the oleuropein in the extract into hydroxytyrosol), and optionally combining the (hydrolysed) olive leave extract with further compounds, to provide the (dermatological) composition. The extract may be further processed with steps known in the art like filtration, concentration, purification, pasteurization, drying, grinding, etc. As indicated above, the further processing may especially also include hydrolysis of the oleuropein (in the extract).

The algae based extract herein is especially an *Arthrospira platensis* extract (*Arthrospira platensis* is formerly known as *spirulina platensis*). This algae is indicated as blue algae or blue-green algae, and is in fact a Cyanobacteria. Herein, the cyanobacteria, and especially the *Arthrospira platensis*, are further indicated as algae. Even more especially, the algae based extract is a high concentrated total extract of the *Arthrospira platensis* algae species (see also below). *Arthrospira Platensis* excretes various biological active compounds during their growth. These compounds are called extracellular polymeric substances (EPS) and appear to have antibacterial activity against *E. coli, S. aureus, S. epidermis, S. typhi, P. aeruginosa, K. pneumonia*. *Arthrospira Platensis* secretes its substances in the forms of sheaths, slimes or capsules, but very little is known about their diversity, mode of synthesis, structure or properties. They prevent unwanted pathogens from binding to human cells, which reduce the infection caused by bacteria. EPS, lipopeptides and tridecapeptides, appear to have moderate antifungal activity against *candida*. These compounds prevent *candida* from binding to human cells on the affected area where the formulation has been applied. Tridecapeptides showed an antifungal activity against *C. Albicans* and lipopeptides against *C. Albicans, C. Glabrata*, and *C. Krusei* (see also below the challenge tests which show the antifungal and antibacterial activity of the algae based extract). *Arthospira platensis* appears to have antiviral activity. A sulphated polysaccharide, called calcium spirulan, was found to inhibit the replication of several enveloped viruses, including Herpes simplex virus type I, measles virus, cytomegalovirus, mumps virus, influenza A, and HIV-I. Hence, the algae based extract or algae material may comprise a polypeptide. The term "polypeptide" may also refer to a plurality of different polypeptides, such as e.g. lipopeptides and tridecapeptides. Especially, the material of algae origin or the algae extract comprises a one or more of a polypeptide and EPS (extracellular polymeric substances). The polypeptide may include one or more of a lipopeptide and a tridecapeptide. The term "polypeptides" may also refer to an oligopeptide. Instead of the term "polypeptide" also the term polypeptide compound may be used.

Non-exhaustive examples of polypeptides, especially lipopeptides, are e.g. glycopeptido lipids, surfactin(s), iturin(s), engycin(s), polymyxins, daptomycin(s), syringomycin(s), anabaenolysin(s), spiroidesin(s), malyngamide(s), puwainaphycin(s), mitsoamide(s), lobocyclamide(s), etc. A lipopeptide may refer to an organic compound of lipids and peptides. Non-exhaustive examples of tridecapeptide are e.g. tolybyssidin(s), such as tolybyssidin A, tolybyssidin B, etc. A tridecapeptide is an oligopeptide having thirteen amino acid residues. Alternative or additionally, also tetradecapeptides, another example of polypeptides, may be present in the material of algae origin. Hence, the polypeptide may include one or more of a lipopeptide, tridecapeptide. Especially, the polypeptide includes polypeptides with at least 10 peptides like tridecapeptide. The polypeptides, especially lipopeptides, may be circular or non-circular, or combinations of circular and non-circular. The material of algae origin, especially the algae extract, and thus also the composition comprising material of algae and olive leaf origin, may especially comprise at least a lobocyclamide and a tolybyssidin.

Especially, as indicated above, as source of algae the algae *Arthrospira platensis* are applied.

The above-mentioned high concentrated extract may include a 10:1 or higher extract, such as a 15:1 or higher, or even a 20:1 or higher extract. This indicates that the concentration of the one or more of EPS and polypeptides is at least 10 times (or 15 or 20, respectively) higher than in the original species.

The extract may e.g. be obtained by a method including treating algae with an aqueous liquid, and providing an alga extract. Hence, in a further embodiment the invention provides said (dermatological) composition wherein the materials of algae origin are especially obtainable by such method including treating algae with an aqueous liquid and providing an alga extract. Also the aqueous liquid used for extraction of the algae may include an alcohol. The alcohol may especially comprise a C2-C8, especially a C2-C6 alcohol, even more especially ethanol. The extraction may be done at elevated temperature, such as in the range of 20-100° C., especially 40-100° C.

Hence, in a further aspect, the invention also provides a method for preparing a (dermatological) composition comprising materials of algae origin, the method comprising treating algae with an aqueous liquid and providing an alga extract, especially comprising at least the polypeptide, and optionally combining the algae extract with further compounds, to provide the dermatological composition. The extract may be further processed with steps known in the art like filtration, concentration, purification, pasteurization, drying, grinding, etc.

In general, the extracts are prepared separately, although optionally also the olive leaf and algae may be combined and then extraction may be executed. In view of the preferred hydrolysis step of the olive leaf oleuropein, a separate extraction of the algae and olive leaf may in general be performed.

The material of algae origin, especially the algae extract, and the material of olive leaf origin, especially the algae extract can be combined. The thus obtained (dermatological) composition may further comprise other components (see also below), which may be added during the extraction(s), and/or during combination, and/or after combination of the materials of algae and olive leaf origin.

Hence, the invention provides in a further aspect a method for preparing a dermatological composition comprising materials of algae origin and olive leaf origin, the composition especially at least comprising a polypeptide and hydroxytyrosol, wherein the method comprises (i) treating algae with the aqueous liquid and providing an algae extract comprising the polypeptide, (ii) treating olive leaf with an aqueous liquid, the aqueous liquid especially also comprising an alcohol, and providing an olive leaf extract, (iii) combining the extracts and optionally combining the extracts with further compounds, to provide the dermatological composition. As indicated above, the method may include a hydrolysis of the olive leaf extract (or optionally of the composition comprising the olive leaf extract).

Hence, the invention especially provides a composition at least comprising (i) a polypeptide, especially a decapetide, and (ii) hydroxytyrosol. Even more especially, the invention provides a dermatological composition comprising materials of algae origin and olive leaf origin, the composition at least comprising a polypeptide and hydroxytyrosol. As indicated above, especially the (dermatological) composition comprises an algae extract and an olive leaf extract.

More especially, the olive leaf extract is an *Olea europaea* leaf extract, obtainable by extraction with a mixture of an alcohol and water, and hydrolysis of the extract, and wherein the algae extract comprises an *Arthrospira platensis* extract, obtainable by extraction with an aqueous liquid. In yet a further embodiment, the (dermatological) composition comprises a weight ratio of oleuropein to hydroxytyrosol of <0.1. Especially, the (dermatological) composition (when comprising the material of olive leave origin) comprises hydroxytyrosol in amount in the range of 0.01-1 wt. % relative to the total weight of the composition. Further, especially the (dermatological) composition further comprises oleic acid, linoleic acid, palmitic acid, a polypeptide (especially one or more of a lipopetide and a tridecapeptide), phycocyanin, and lipids.

Especially, the (dermatological) composition is a dermatological composition for use in the treatment and/or prevention of a dermatological microbiological infection. For instance, the (dermatological) composition may especially be a dermatological composition for use in the treatment and/or prevention of a skin infection or a nail infection selected from the group consisting of nail fungus and Athlete's foot. However, the (dermatological) composition may also be a dermatological composition for use in the treatment of a wound (such as a wound spray). In yet a further embodiment, the (dermatological) composition is a dermatological composition for use in the treatment of chickenpox (and/)or acne. As will be clear to a person skilled in the art, the (same) dermatological composition may be used for different applications and may (thus) be indicated for different applications.

Herein, the term "dermatological" and similar terms especially relate to hair, nails, skin, even more especially to nail and skin. A dermatological composition is a composition that is suitable to be applied to the skin or the nails. This term is known to the person skilled in the art. The (dermatological) composition herein may especially be applied for (use in) the treatment and/or prevention of the herein indicated illnesses like nail fungus, Athlete's foot, acne, chickenpox, etc. The (dermatological) composition herein may therefore also be used in a prophylactic treatment.

Athlete's foot is a very common skin infection of the foot sole and between the toes caused by fungal infection. Athlete's foot is also called tinea pedis. The fungi that most commonly cause athlete's foot are *Trichophyton* and *Candida*. When the feet or other areas of the body stay moist, warm, and become irritated, fungus can thrive and infect the upper layers of the skin. The ringworm fungus (called tinea) causes athlete's foot. Tinea can be found on many locations, including floors in gyms, locker rooms, swimming pools, nail salons, airport security lines, and in socks and clothing. The fungus can also be spread directly from person to person or by contact with these objects. Most people acquire fungus on the feet from walking barefoot on areas where someone else with athlete's foot has walked. Some people are simply more prone to this condition while others seem relatively resistant to contracting it. However, proper growing conditions (a warm, moist environment) are essential for the fungus to infect the skin. Up to 70% of the population may have athlete's foot at some time during their lives. Some individuals are inherently more prone to recurrences during their lifetime. Most individuals with athlete's foot have no symptoms at all and do not even know that they have an infection. Many may think they simply have dry skin on the soles of their feet. Common symptoms of athlete's foot typically include various degrees of itching and burning. The skin may frequently peel, and in particularly severe cases, there may be some cracking, pain, and bleeding as well. Rarely, athlete's foot can blister (called bullous tinea pedis). Most cases of athlete's foot are barely noticeable with symptoms as a just slightly dry, flaky skin. More extensive athlete's foot may look like red, with peeling and dry skin areas on one or both soles of the feet. Sometimes the dry flakes may spread onto the sides and tops of the feet. Most commonly, the rash is localized to just the bottoms of the feet. The space between the fourth and fifth toes also may have some moisture, peeling, and dry flakes. There are three common types of athlete's foot: 1. "Moccasin" type (feet's sole); 2. "Inter-digital" type (between the toes); 3. Inflammatory type or blistering.

Onychomycosis (OM) refers to a fungal infection that affects the toenails or fingernails. Onychomycosis may involve any component of the nail unit, including the nail matrix, nail bed, or nail plate. The primary fungi that cause onychomycosis are *Trichophyton rubrum* and *Trichophyton mentagrophytes*. They are dermatophytes (fungi that infect hair, skin, and nails) and feed on keratinized (nail) tissue. The infections they cause are normally confined to the nails, but occasionally spread to the surrounding skin. The incidence of onychomycosis has been reported to be 2-13% in North America. Onychomycosis accounts for half of all nail disorders, and it is the most common nail disease in adults. Toenails are much more likely to be infected than fingernails. Thirty percent of patients with a cutaneous fungal infection also have onychomycosis. The incidence of onychomycosis has been increasing, owing to such factors as diabetes, immunosuppression, and increasing age. Studies in the United Kingdom, Spain, and Finland found prevalence rates of onychomycosis to be 3-8%. The prevalence of onychomycosis is higher (25%) in patients with HIV. Several studies show that prevalence of onychomycosis increases with age, reasons for which may include poor peripheral circulation, diabetes, repeated nail trauma, longer exposure to pathogenic fungi, sub optimal immune function, inactivity or inability to cut toenails or maintain good foot care. Onychomycosisis is classified clinically as distal and lateral subungual onychomycosis (DLSO), superficial white onychomycosis (SWO), proximal subungual onychomycosis (PSO), candidal onychomycosis and total dystrophic onychomycosis. DSLO accounts for the majority of cases and it is almost always due to dermatophyte infection. It affects the hyponychium, often at the lateral edges initially, and spreads proximally along the nail bed resulting in subungual hyperkeratosis and onycholysis although the nail plate is not initially affected. DLSO may be confined to one side of the nail or spread sideways to involve the whole nail bed, and progresses relentlessly until it reaches the posterior nail fold. Eventually the nail plate becomes friable and may break up, often due to trauma, although nail destruction may be related to invasion of the plate by dermatophytes that have keratolytic properties. Examination of the surrounding skin will nearly always reveal evidence of tinea pedis. Toenail infection is an almost inevitable precursor of fingernail dermatophygosis, which has similar clinical appearance although nail thickening is not as common. PSO, without evidence of paronychia, is an uncommon variety of dermpatophyte infection often related to intercurrent disease. Immunosuppressed patients, notably those who are human immunodeficiency virus-positive, may present with this variety of dermatophyte infection; conditions such as peripheral vascular disease and diabetes may also be present in this way. Evidence of intercurrent disease should therefore be considered in a patient with PSO. Infection of the nail apparatus with *Candida* yeasts may present in one of four ways: (i) chronic paronychia with secondary nail dystrophy; (ii) distal nail infection; (iii) chronic mucocutaneous candidiasis; and (iv) secondary candidiasis. Chronic paronychia of the fingernails generally only occurs in patients with wet occupations. Swelling of the posterior nail fold occurs secondary to chronic immersion in water or possibly due to allergic reactions to some foods, and the cuticle becomes detached from the nail plate thus losing its water-tight properties. Microorganisms, both bacteria and fungi, enter the subcuticular space causing further swelling of the posterior nail fold and further cuticular detachment, i.e. a vicious circle. Infection and inflammation in the area of the nail matrix eventually lead to a proximal nail dystrophy. Distal nail infection with *Candida* yeasts is uncommon and virtually all patients have Raynaud's phenomenon or some other form of vascular insufficiency. It is unclear whether the underlying vascular problem gives rise to onycholysis as the initial event or whether yeast infection causes the onycholysis. Although candidal onychomycosis cannot be clinically differentiated from DLSO with certainty, the absence of toenail involvement and typically a lesser degree of subungual hyperkeratosis are helpful diagnostic features. Chronic mucocutaneous candidiasis has multifactorial etiology leading to diminished cell-mediated immunity. Clinical signs vary with the severity of immunosuppression, but in more severe cases gross thickening of the nails occurs, amounting to a *Candida granuloma*. The mucous membranes are almost always involved in such cases. Secondary candidal onychomycosis occurs in other diseases of the nail apparatus, most notably psioriasis. Onychomychosis is not life threatening, but it can cause pain, discomfort, and disfigurement and may produce serious physical and occupational limitations. Psychosocial and emotional effects resulting from onychomycosis are widespread and may have a significant impact on quality of life.

Chickenpox is a viral infection in which a person develops extremely itchy blisters all over the body. It is caused by the varicella-zoster virus, a member of the herpes virus family. Chickenpox can be spread very easily from one person to another. You may get chickenpox from touching the fluids from a chickenpox blister, or if someone with the disease cough or sneezes near you. Patients with mild symptoms of the illness can be contagious as well. A person with chickenpox becomes contagious 1 to 2 days before the blisters appear and remain contagious until all the blisters have crusted over. Most cases of chickenpox occur in children younger than 10 years old, in temperate climates of the Northern Hemisphere, varicella occurs mainly in the period from late winter to early spring. Secondary attack rates reach close to 90% in susceptible household contacts. Once a case has occurred in a susceptible population, it is very hard to prevent an outbreak. Almost every human being experiences the disease. Most children with chickenpox have the following symptoms before the rash appears: (1) fever; (2) headache; and (3) stomach-ache. The chickenpox rash occurs about 10 to 21 days after coming into contact with someone who has the disease. The average child develops 250 to 500 small, itchy, fluid-filled blisters and/or red spots on the skin. The most likely location of the blisters is the face, middle part of the body or scalp. Most blisters will not leave scars unless they become infected with bacteria. This can be induced by scratching due to the itchiness. The current treatment is based on a topical disinfectant or an anti-itch powder based on menthol. The topical disinfectant is aimed at eradicating bacteria by use of a biocidal ingredient. Therefore, this treatment is classified as drug/biocide. The anti-itch powder does not provide treatment against bacteria or promote wound healing. It is solely based on symptom relief and reducing itching. These kinds of treatment are classified as either drug or medical device.

Acne vulgaris (acne) is one of the most common human skin diseases worldwide characterized by areas of skin with seborrhea, comedones, papules, pustules, nodules and possibly scarring. It mostly affects the face area, but it can also appear in the upper-chest and back. Bacteria play a role in worsening acne, by growing in the clogged, oily sebaceous pores and causing inflammatory responses. *Propionibacterium acnes, Staphilococcus epidermidis*, are the main colonizer strains. Current treatment of mild forms of acne involves killing *P. acnes* with bactericidal agents such as benzoyl peroxide and oral or topical antibiotics, all of which indiscriminately kill many bacterial species and disrupt the normal balance of the skin microflora. Long-term use of antibiotics also leads to resistant strains of *P. acnes*. A healthy skin pore is composed of a sebaceous gland that secretes the right amount of sebum, an oily substance that lubricates the hair follicle and skin itself. Sebum production is regulated by hormones. When there is hormonal unbalance, excessive sebum can clog the pore, and, the bacteria, normally living on the skin surface, can spread in the sebaceous pore and multiply, causing further inflammation.

The resulting bacterial spread, and the triggered inflammatory response in the pore, is ultimately responsible for acne severity.

The use in the treatment of wounds may especially relate to small wounds like (small) cuts, (small) burns and insect bites. The composition may also be used in the treatment of an abrasion (wound) or small burn (wound). Especially, the wound to be treated occupies less than 5%, especially less than 1%, of the total body surface area (TBSA) (referring to a single or compact wound). The composition of the invention may prevent scarring, may provide a soothing effect upon contact, may prevent bacterial infections, and/or may relieve pain and discomfort (decreases infection risks).

It surprisingly appears that the (dermatological) composition may especially a (dermatological) composition for use in the treatment and/or prevention of one or more of *P. aeruginosa*, *S. aureus*, *C. albicans*, *A. brasiliensis* and *E. hirae*. The composition effectively eliminates such bacteria, or at least substantially reduces the bacterial count of such bacteria when applied on the skin (including a skin wound). Amongst others for this reason the composition may especially be a dermatological composition for (i) use in the treatment and/or prevention of one or more of nail fungus and Athlete's food, and/or (ii) the treatment of one or more of a wound, chickenpox, and acne.

The composition may be available in the form of e.g. a liquid, a foam, a cream, paste, powder, etc. Hence, especially the composition is topical composition, such as a cream, a foam, a gel, a lotion and an ointment, etc. The composition may be applied in different ways, like e.g. as spray, as cream, as stick, as pen, etc. further the composition may also be available as coating or impregnated material in or on a bandage, a patch, a plaster, like an adhesive bandage, or a wound dressing, etc. for further information on applicators see also below.

Further, the compositions described herein, especially the (dermatological) composition comprising materials of algae origin and olive leaf origin, may include other ingredients, not originally from algae and/or olive leaf.

For instance, the composition may further include one or more excipients. An excipient is especially an inactive substance formulated alongside the active ingredient(s) (which can be found in the material of algae and/or olive leaf origin) of a product or medication, for the purpose of bulking-up formulations that contain such active ingredient(s). Excipients may for instance also be indicated as filler or diluent. Excipients may e.g. include one or more of binders, coatings, disintegrates, fillers, flavors, colorants, lubricants, glidants, sorbents, preservatives, sweeteners, etc. etc.

The composition may further e.g. comprise silk fibroin. Silk fibroin is a protein derived from hydrolization of silk fibers, naturally secreted by silk work *Bombyx mori*. Silk fibroin has diverse applications in the biomedical field, which can be attributed to its high tensile strength, controllable biodegradability, non-cytotoxicity, low-antigenicity and non inflammatory characteristics. The use of silk fibroin extract can aid the healing process during regeneration and repair of normal and functional nail tissue. The composition may further (also) comprise pentylene glycol. Pentylene glycol is used as moisturizing agent. It is a colorless liquid, very low in odor, that is both water and oil-soluble. Due to its unique molecular properties, including a well separated charge distribution pattern, pentylene glycol performs its moisturizing activity much better than comparable chemicals, i.e. propylene glycol. The composition may further (also) comprise dimethyl isosorbide. Dimethyl isosorbide is a delivery enhancer which can place active ingredients where they are needed most and it is thus used as penetrating system for the keratinous nail layer. Dimethyl isosorbide is a colorless liquid with excellent solvent properties. It enhances delivery of actives in the upper layers of the epidermis without promoting the product into the bloodstream. Moreover, dimethyl isosorbide improves stability of formulations, even those that are susceptible to hydrolysis and transesterification. The one or more of silk fibroin, pentylene glycol and dimethyl isosorbide may especially be applied in a composition for the treatment and/or prevention of nail fungus. For instance, they may be available in a nail (fungus) pen.

The composition may further e.g. comprise urea (or carbamide). Urea is an organic compound with the chemical formula $CO(NH_2)_2$. Urea-containing creams are widely known and used as topical dermatological products to promote rehydration of the skin. It further appears that urea can be indicated for psoriasis, xerosis, onychomycosis, ichthyosis, eczema, keratosis, keratoderma, corns and calluses. Its use in the e.g. the treatment and/or prevention of Athlete's foot, such as in an Athlete's foot Pen (and/or Athlete's foot spray) may be intended as moisturizer agent for dry skin affected by athlete's foot. The composition may further e.g. comprise allantoin. Allantoin is a chemical compound with formula $C_4H_6N_4O_3$. It is also called 5-ureidohydantoin or glyoxyldiureide. It is a diureide of glyoxylic acid. It is used for its moisturizing properties since it increases the water content of the extracellular matrix. It also enhances the desquamation of upper layers of dead skin cells, favoring a faster healing process of damaged skin. The composition may further e.g. comprise panthenol. Panthenol is the alcohol analog of pantothenic acid (vitamin B5), and is thus a provitamin of B5. In organisms it is quickly oxidized to pantothenate. In e.g. the treatment and/or prevention of Athletes's foot, such as in an Athlete's Foot Pen (and/or Athlete's foot spray), panthenol may be used as a humectant, emollient and moisturizer. The one or more of urea, allantoin, and panthenol may especially be applied in a composition for the treatment and/or prevention Athlete's foot, such as in an Athlete's foot pen (and/or Athlete's foot spray).

The composition may further e.g. comprise glycerin. Glycerin (or glycerol) is a polyol compound. It is a colorless, odorless, viscous liquid that is widely used in pharmaceutical formulations. Glycerol has three hydroxyl groups that are responsible for its solubility in water and its hygroscopic nature. The glycerol backbone is central to all lipids known as triglycerides. Glycerol is sweet-tasting and of low toxicity. Glycerol is used (in medical and pharmaceutical and personal care preparations), mainly as a means of improving smoothness, providing lubrication and as a humectant. Glycerin may especially be applied in a composition for the treatment and/or prevention Athlete's foot, such as in an Athlete's foot spray (and/or Athlete's foot pen).

The composition may further e.g. comprise Pemulen®. The composition may further e.g. comprise one or more of zinc oxide, menthol, bisalol, paraffin, laureth-9, penthylene glycol, Polyglyceryl-3 methylglucose distearate, and citric acid. Pemulen® a polymeric emulsifier which has the capability to absorb oil and water, forming a very stable oil-in-water emulsion. Zinc oxide is a white opaque pigment which prevents bacterial growth and offers UV protection. Menthol may provide a cooling effect, which diverts one's attention away from itching. Due to the cooling effect, the composition, such as when used as spray, may also be effective for the relief of sunburn as well. Bisalol may be used as a conditioning agent with soothing and anti-irritating properties, accelerating wound healing. Laureth-9 is an emulsifier with anti-itching properties and liquid paraffin can be used as lubricant; both ingredients calm, soften and protect de skin. Penthylene glycol is a moisturizer which facilitates the natural healing process. Polyglyceryl-3 methylglucose distearate may be used as an emulsifier which forms stable emulsions with all common oils and fats. Citric acid is a natural preservative and is used to lower the pH. Pemulen® and/or one or more of zinc oxide, menthol, bisalol, paraffin, laureth-9, penthylene glycol, Polyglyceryl-3 methylglucose distearate, and citric acid may especially be applied in a composition for the treatment of a wound (and/) or chickenpox, such as especially in a wound spray or a chickenpox spray.

In yet a further aspect the invention provides a (dermatological) composition comprising (at least) materials of (1) blue algae (or cyanobacteria) origin, and (2) olive leaf origin, the composition especially at least comprising a polypeptide and hydroxytyrosol. It was surprisingly found that the combination of the material of blue algae origin (especially including amongst others beneficial polypeptides) and the material of olive leaf origin (including the hydroxytyrosol having beneficial properties) provides a synergistic effect and appeared to be effective against microorganisms, such as bacteria, that could not be (well) treated with an algae composition or an olive leaf composition alone. Especially, the blue algae comprises *Arthrospira platensis*. Hence, the material of algae origin or the algae extract may comprise material of *Arthrospira platensis* origin or *Arthrospira platensis* extract, respectively. Other cyanobacteria may also be of interest.

The invention further relates to an applicator device comprising a composition as defined herein. This applicator device is especially a device with a container containing the composition(s) as described herein and is further especially configured to release part of the composition upon a user action, such as sweeping or pressing an composition access part of the applicator device to the skin, or spraying the composition with a spray applicator device. Hence, in a specific embodiment the applicator device is a spray applicator device and the composition is in an aqueous state in a container comprised by the applicator device. In an embodiment, the spray applicator device may include an aerosol powder spray (applicator device). Other applicator devices may include a roll on applicator. In yet another specific embodiment, the applicator device is a pen applicator device, and the composition is topical composition, such as a cream, a foam, a gel, a lotion and an ointment. Other options may also be possible, like a paste or powder. The pen applicator device may especially be a spot pen (applicator device). Further, the composition may be included in a tube. Hence, also a tube including the composition as described herein is provided.

The term "substantially" herein, such as in "substantially free" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The devices herein can amongst others be described during operation. As will be clear to the person skilled in the art, the invention is not limited to methods of operation or devices in operation. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage. The invention further pertains to a method or process comprising one or more of the characterizing features described in the description. The various aspects discussed in this patent can be combined in order to provide additional advantages. Furthermore, some of the features can form the basis for one or more divisional applications.

DETAILED DESCRIPTION OF THE EMBODIMENTS AND EXPERIMENTS

Below, first embodiments and examples are described in relation to a use in the treatment of Athlete's foot. However, the below embodiments and examples are not limited to only the Athlete's foot application. The embodiments and examples are especially described in relation to a pen. This is an applicator device with a tip (the composition access part of the applicator device), which when contacted with the skin release the composition. This can e.g. be due to the fact that the composition sticks to the skin. However, the invention is not limited to this applicator device embodiment.

For instance, the Athlete's foot pen is a product that treats and prevents Tinea Pedis, without the side effects of pharmacological products, which may cause irritation and contact dermatitis. Athlete Foot Pen is amongst others intended for the treatment of a fungal infection between the toes. The applicator is adjusted to the product's purpose; the solution can be applied precisely on the infected area between the toes. The formulation in the Athlete's foot pen appears to form a physical film layer on the skin that prevents further spreading of the fungus between the toes. The physical layer, which contains the herein described composition and may create a hostile environment for fungal species, which results in inhibition of growth and successful eradication of the causative fungus.

One in vivo test and two in vitro tests have been completed to evaluate the efficacy of the Athlete Foot pen. The efficacy of the Athlete's Foot formulation was assessed in an in vivo test. Objective of the study was the assessment on the appearance of tinea pedis skin after a treatment of 4 weeks based on visual skin improvement compared to the starting point. This study was conducted under the supervision of a dermatologist affiliated to one of the largest dermatology centers in Europe. In total 23 subjects with tinea pedis participated in the study. The treatment with the formulation was performed on the affected area. Subjects were instructed to use Athlete's Foot formulation twice a day for a period of four weeks, morning and evening. They were instructed to carefully clean and dry the affected area prior to application of an Athlete's Foot product to the skin and dry for 1 minute in order to ensure good penetration throughout the whole affected epidermis. The test areas were examined visually and the subjects were interviewed in regard to their perception.

No unforeseen events happened. All subjects finished the study correctly and completely. The results contain the opinion of the dermatologist and patient's assessment. After one week, patients observed improvement in the foot skin condition: skin was less irritated, inflammatory regions in between toes were significantly decreased, and the foot looked overall healthier. After four weeks of treatment, treated skin showed a significant improvement, 68% of volunteers were cleared of the symptoms associated with athlete foot. Bacteria and fungi were eradicated from the epidermis of the subjects. In total 83% of the subjects indicated to be satisfied with the product. Findings of this study indicate that Athlete's Foot formulation is effective and safe in treating moderate to severe tinea pedis. Athlete's Foot formulation provides a clear efficacy to improve the visual appearance of the treated skin in all subjects compared to the starting point. The subjects described a positive effect of the product. Subjects didn't experience any side effects during the treatment. These encouraging findings suggest that Athlete's Foot products are useful in an effective treatment regimen for tinea pedis.

The olive leaf extract and the algae extract have both been tested for their antimicrobial activity on the bacteria *Staphylococcus aureus*, and the fungi *Candida albicans* and *Aspergillus brasiliensis* during a challenge test. The amount of pathogens were measured at baseline (0 hours). Afterwards, the olive leaf extract and the algae extract have been added to the colony forming unit. Finally, after 24 hours, the amount of pathogens in the colony forming unit have been measured once more. The olive leaf extract showed a decrease in *S. aureus*. The algae extract showed a decrease in *S. aureus*, *C. albicans* and *A. brasiliensis*. In other words, the olive leaf extract showed an antibacterial activity and the algae extract showed an antibacterial and antifungal activity. These results are shown below.

Results Laboratory Challenge Tests:

| Olive leaf extract | | | |
|---|---|---|---|
| Time (hours) | 0[1] | 0 | 24 |
| *S. aureus* | | | |
| CFU[2] count ($^{10}$log) | 5.8 | 5.7 | <1.0 |
| Reduction ($^{10}$log) | — | 0.1 | 4.8 |
| *P. aeruginosa* | | | |
| CFU[2] count ($^{10}$log) | 5.2 | 4.9 | 4.1 |
| Reduction ($^{10}$log) | — | 0.4 | 1.2 |
| *C. albicans* | | | |
| CFU[2] count ($^{10}$log) | 5.8 | 5.8 | 5.9 |
| Reduction ($^{10}$log) | — | 0 | 0 |
| *A. brasiliensis* | | | |
| CFU[2] count ($^{10}$log) | 5.2 | 5.3 | 4.6 |
| Reduction ($^{10}$log) | — | −0.1 | 0.6 |

[1]Inoculum count;
[2]CFU: Colony Forming Unit

| Algae extract | | | |
|---|---|---|---|
| Time (hours) | 0[1] | 0 | 24 |
| *S. aureus* | | | |
| CFU[2] count ($^{10}$log) | 5.2 | 5.1 | 1.0 |
| Reduction ($^{10}$log) | — | 0.1 | 4.2 |
| *P. aeruginosa* | | | |
| CFU[2] count ($^{10}$log) | 5.7 | 5.1 | 3.4 |
| Reduction ($^{10}$log) | — | 0.6 | 2.3 |
| *C. albicans* | | | |
| CFU[2] count ($^{10}$log) | 5.7 | 5.9 | 1.0 |
| Reduction ($^{10}$log) | — | −0.2 | 4.7 |
| *A. brasiliensis* | | | |
| CFU[2] count ($^{10}$log) | 6.0 | 5.9 | 1.0 |
| Reduction ($^{10}$log) | — | 0.1 | 5.0 |

[1]Inoculum count;
[2]CFU: Colony Forming Unit

The combination of the two products shows an increased efficacy against bacteria and fungi. The combination is effective against all tested bacteria and fungi:

| Composition comprising both extracts | | | | |
|---|---|---|---|---|
| Time (hours) | 0[1] | 0 | 24 | 96 |
| *P. aeruginosa* ATCC 9027 | | | | |
| CFU[2] count ($^{10}$log) | 5.9 | <1.3 | <1.3 | 1.0 |
| Reduction ($^{10}$log) | — | 4.6 | 4.6 | 4.9 |
| *S. aureus* ATCC 6538 | | | | |
| CFU[2] count ($^{10}$log) | 5.9 | 1.6 | <1.3 | 1.0 |
| Reduction ($^{10}$log) | — | 4.3 | 4.6 | 4.9 |
| *C. albicans* ATCC 10231 | | | | |
| CFU[2] count ($^{10}$log) | 5.8 | 4.5 | <1.3 | 1.0 |
| Reduction ($^{10}$log) | — | 1.3 | 4.5 | 4.8 |
| *A. brasiliensis* ATCC 16404 | | | | |
| CFU[2] count ($^{10}$log) | 6.0 | 5.9 | <1.3 | 1.0 |
| Reduction ($^{10}$log) | — | 0.1 | 4.7 | 5.0 |
| *E. hirae* ATCC 10541 | | | | |
| CFU[2] count ($^{10}$log) | 6.1 | 5.7 | <1.3 | 1.0 |
| Reduction ($^{10}$log) | — | 0.4 | 4.8 | 5.1 |

[1]Inoculum count;
[2]CFU: Colony Forming Unit

Treatments were well tolerated in all the reviewed studies. It was observed that the olive leaf extract and the algae extract caused no irritation or patient complaints. Another area considered in this review was the safety of the excipients used. The conclusion is that the composition of (athlete's foot) composition with regard to contents of all other ingredients in the formulation is safe to be used on the affected foot skin.

Comparable products available in the market for athlete's foot treatment and prevention have the strong disadvantage of containing ingredients that do not act mechanically on the fungus-infested skin. The present composition and applicator device, such as the athlete's foot pen, is the first of-its-kind product that efficiently treats and prevents athlete's foot without any known side effects and exerting its function without pharmacological, immunological or metabolic means. It can be concluded that the ingredients in the athlete's foot pen can be efficiently used as topical treatment on feet affected by tinea pedis (athlete's foot). The athlete's foot pen formulation with olive leaf extract and algae extract is effective in inhibiting growth and eradicate dermatophytes responsible for athlete's foot, as demonstrated by both laboratory microbiological studies and in preliminary data on ongoing pre-clinical in-house study on patients affected by tinea pedis.

Below, embodiments and examples are described in relation to a use in the treatment of nail fungus. However, the below embodiments and examples are not limited to only the nail fungus application. The embodiments and examples are especially described in relation to a pen. This is an applicator device with a tip (the composition access part of the applicator device), which when contacted with the nail release the composition. This can e.g. be due to the fact that the composition sticks to the nail. However, the invention is not limited to this applicator device embodiment.

Especially, the nail pen is a two piece hard pen with e.g. disposable cellulose tips containing a liquid formulation intended to be applied on fungi-infested nail in order to treat onychomycosis and restore normal nail tissue. The liquid formulation of the nail pen is composed of olive leaf extract, algae extract, silk fibroin extract, pentylene glycol, and dimethyl isosorbide. The average volume of a filled pen is 4 ml, and total pen weight is approximately 19 g (Attachment-B, Table 1-Qualitative and Quantitative composition of nail pen). Nail pen is risk classified as a Medical Device according to the Medical Device Directive, Annex IX, Rule 4, paragraph 3. This classification means that the product belongs to all non-invasive devices which come in contact with injured skin which are in Class IIa. The nail pen is applied directly on the infected nail only. The nail pen should especially be applied on onychomycotic nail area twice a day, for a period of 30 days. In case of persistent infection, it is advised to consult a general practitioner for other treatments options. If taken according to directions, the label claims that nail pen is especially intended to one or more of (i) treating and preventing onychomycosis; (ii) countering a yeast infection; and (iii) maintaining healthy nails.

One clinical in vivo study demonstrates the efficacy of the nail pen, which is a medical device for topical application to treat and prevent fungal infection of the nails, containing the olive leaf extract and the algae extract as active medical ingredients.

In total fifty volunteers from both sexes were selected and subsequently included in the study. The age varied from 18 to 65 years and they presented with distal or lateral subungual onychomycosis of at least one toe. Only onychomycosis involving between 50 and 100% of the nail plate were included. The free and explained consent form was read and signed by all the volunteers, prior to the commencement of the study. All the patients were submitted to direct mycological examination and samples were taken to determine the cause of onychomycosis, prior to the start of the study. The nail area was cleaned with ethanol spray and nail fragment was clipped off, and collected in a sterile Eppendorf tube. In between each sample, the clippers were wiped clean with 70% ethanol. From each nail at least two fragments were collected.

One fragment was used for microscopic examination with KOH preparation to identify fungal structures. The other fragments were used for cultures in Bacto Agar (Becton Dickinson), Mycosel Agar (BBL). The isolated strains were analyzed microscopically. All microbiologic analyses were done by a certified laboratory. Only when the tests were positive for onychomycosis and the volunteers' eligibility were confirmed, they were entered into the study. An initial assessment questionnaire was filled in by the principal investigator for each individual volunteer that would serve as the parameter for the evaluation of the treatment.

The volunteers received the nail pen and instruction on how to use the pen. Volunteers were instructed to carefully file the top of the affected nail, once a week prior to the application of the nail pen. The nail pen, containing the olive leaf extract and the algae extract, was applied twice a day, in the morning and in the evening, for a period of six weeks. The nail pen had to be applied to the whole nail plate and left to dry for one minute. Should the symptoms of onychomycosis disappear before the termination of the study, volunteers were asked to continue with single treatment per day to prevent re-infection.

After 28 days an assessment of the therapeutic effect was performed by mycological examination and culture to determine the reduction of the causative organisms. At the end of the study the nails of the volunteers were evaluated and submitted to a final measurement. The primary efficacy variable was therapeutic success, defined as clinical improvement of complete nail health and the mycological cure (negative culture).

In total fifty patients completed the study successfully. Of these fifty patients 21 were men (42%) and 27 were women (54%), two did not specify there gender (4%). All volunteers were aged between 18 and 65 years. The nail material was collected at the beginning (t=0), intermediate (t=28 days) and the end of the study (t=42 days). Initial testing revealed that main causative organisms were *Candida*, and 7 patients (14%) had accompanying paronychia (caused by *Staphylococci* and *Streptococci* infection). In the case of 5 patients (10%) the type of the fungi strain was not identified and we suspect that it was one of the most common dermatophytes that cause onychomycosis.

During the entire treatment the patients were asked to keep a diary related to the treatment and the improvements. Patients observed significant improvement in the nail condition: lunular area was less irritated, inflammatory regions in the nail plate and the proximal and lateral nail folds were significantly decreased. Overall the volunteers were very positive about the product performance and no side effects were reported. In the evaluation 41 patients (82%) declared high product satisfaction. The majority of the volunteers experienced a relief and observed improvement of nail structure after one week of treatment.

After six weeks the study was completed. The nails were clipped off and sent for microbiological analysis. The nails were better shaped, no redness or irritation around eponychium was observed. Patients observed improved hardness and strength of their nails. Furthermore, 43 patients (86%) showed that Onychomycosis was cleared from their nails. The microbiological results of the remaining seven patients (14%) still had moderate levels of *Candida* infection. In the case of the two patients with accompanying paronychia, bacterial infection was cleared completely. The lunular and eponychium area returned to their natural color, the proximal and lateral folds were less painful and showed decreased inflammatory levels.

The fifty volunteers were requested to complete a questionnaire. For forty out of the fifty volunteers it was not the first incidence of onychomycosis. They suffered prior to the study and sought medical advice. Some of them were successfully treated with other treatments, which were long lasting, sometimes with associated adverse-effects. Therefore these patients were eager to try an alternative treatment. The majority: thirty out of fifty patients had a history of disease—to a maximum of two years. Twenty patients (40%) had a history of disease longer than two years, and five of them (10%) for almost five years. Almost all volunteers declared overall satisfaction with the product. Most of them would recommend this product. No adverse effects were reported.

In total fifty volunteers with onychomycosis accompanied in seven cases (14%) with paronychia (bacterial infection) and five patients (10%) with unknown fungus infection treated their nails for six weeks with the nail pen containing olive leaf extract and algae extract. Within one week the majority of the volunteers observed noticeable difference in the nail condition. At the end of the study 86% of the patients were cleared of onychomycosis, and all (7) patients with paronychia were found to have no more signs of bacterial infection. The remaining seven patients (14%) showed a decrease in the level of causative organisms. However, onychomycosis was not completely healed. We conclude that the reason for this is the prolonged disease history and that longer treatment time would be required in order to clear the onychomycosis. All volunteers showed overall high satisfaction with the product and would use the nail pen again if given such opportunity. No adverse effects were reported. Concluding, this in vivo efficacy study shows that the nail pen containing olive leaf extract and algae extract is effective against a broad spectrum of fungi and bacteria. Patients observed improvement in nail appearance within the first week of treatment. Therefore, the ail pen offers a rapid and safe treatment alternative for onychomycosis, compared to other products that are already on the market.

In laboratory tests, we assessed the efficacy of the nail pen formulation on the growth of different yeasts and bacteria. The different strains that were tested were: *Candida albicans, Pseudomonas aeruginosa, Staphylococcus aureus,* and *Enterocuccus hirae*. Of each strain a culture was prepared and the number of cells/ml was determined. The concentration was adjusted to 102 to 103 cfu/ml. The strain was then suspended in buffered pepton water. Of each strain, 9 ml were added to 8 sterile tubes. To each tube 1 ml of formula was added. The formula was filter sterilized with filters with pre size 0.22 um before it was added to each strain. The samples were stored for 96 hours at 25° C. As negative control, formula without micro-organisms was used. After incubation of 96 hours, a sample was taken to determine the amount of cells, analyzed by aerobic plate count conform to ISO 4833. Results showed that nail pen formulation containing 0.4% olive leaf extract was able to inhibit and kill all micro-organisms taken into account, thus proving its efficacy as antifungal and antibacterial agent.

Treatments were well tolerated in all the reviewed studies. It was observed that olive leaf extract caused no irritation or patient complaints. Also, being an all-natural product, it is the opinion of the reviewer that there are no unknown or serious effects that have been discovered.

Another area considered in this review was the safety of the excipients used. The conclusion is that the composition of nail pen with regard to contents of dimethyl isosorbide and pentylene glycol is safe to be used on the nail.

The clinical efficacy of nail pen has been tested for in vitro activity on different strains of fungi and bacteria compared to other available products. The effect of the nail pen formula against competitor products was tested on cultures of: (i) *Candida albicans*; (ii) *Pseudomonas aeruginosa*; (iii) *Enterococcus hirae*; and (iv) *Staphylococcus aereus*.

The experiment on efficacy was designed as follows: (1) Positive control: bacteria grown without addition of any formula; (2) Negative control: sample of the nail pen (of the invention), Ref. M1, Ref. DS1 and Ref. N1 grown in the medium (for possible contamination); (3) of each strain, 9 ml was used and 1 ml of the formula was tested; (4) 1 ml of formula was added to each tube. The samples were stored for 96 hours, *Pseudomonas, Staphylococcus* and *Enterococcus hirae* at 37° C., *Candida* at 25° C. After 96 hours a sample was taken to determine the amount of cells. This was analyzed by aerobic plate count conform ISO 4833 (by counting colonies=cfu/ml).

From the data thus obtained it was be concluded that nail pen, Ref. N1 and Ref. DS1 were effective against all tested microbial species within 96 hours. The nail pen was slightly more efficient than Ref. N1 in inhibiting the growth of *C. albicans*. Ref. M1 had no anti-microbial effect within 96 hours. Although both the nail pen and Ref. N1 both efficiently inhibit microbial and fungal growth, Ref. N1 contains tea tree oil and lavender oil, which have been reported to have systemic effects. Therefore Ref. N1 should not be used in children pregnant or lactating women. Our study also shows that Ref. DS1 is effective in inhibiting growth of fungi and bacteria that might infect the nail. These results were expected since Ref. DS1 is formulated with harsh chemicals, which could cause serious side effects like severe blistering of the skin or irritation. The nail pen has no reported side effects, thus making it very efficient and a safer product to treat and prevent onychomycosis.

Below, embodiments and examples are described in relation to a use in the treatment of chickenpox. However, the below embodiments and examples are not limited to only the chickenpox application. The embodiments and examples are especially described in relation to a spray. However, the invention is not limited to this applicator device embodiment.

The chickenpox spray (a vacuum spray) is classified as a Medical Device. A medical device is a product, which is used for medical purposes in patients, in diagnosis, therapy or surgery. If applied to the body, the effect of the medical device is primarily physical, in contrast to pharmaceutical drugs, which exert a pharmacological, immunological or metabolic effect. The vacuum spray applicator allows wide distribution of micro-droplets of the liquid formula across the effected skin surface without touching the infected blisters. The chickenpox spray is designed as a topical medical device that forms a protective physical layer on the skin that acts as a barrier providing a cooling effect that reduces the itchiness. The physical layer allows the small wounds to stay moist, which promotes the healing of the wounds. The formulation contains the active ingredients olive leaf extract and algae extract which inhibit bacterial growth by creating a hostile environment for bacteria that can grow easily in wounds that are scratched due to itchiness. By preventing bacterial infection, scarring caused by the infected small wounds is prevented.

Biocompatibility results indicate an excellent safety profile. Chickenpox spray is well tolerated. Studies show the benefit/risk ratio of this product and its component as positive. No known side effects were found. The evaluation performed indicates that the products are safe and effective and fulfil its intended purpose as a medical device. The product performs according to its labelled claims. Based on the above evidence the following statements are being claimed by the chickenpox spray: (i) treating itching and wounds cause by chickenpox; (ii) treating and preventing secondary infection cause by scratching; and (iii) prevents scarring caused by secondary infection.

Below, embodiments and examples are described in relation to a use in the treatment of acne. However, the below embodiments and examples are not limited to only the acne application. The Embodiments and examples are especially described in relation to a cream.

Acne cream may for instance be used in a treatment in combination with a cleanser. The acne cream contains the herein described composition. The product is effective against the causing factors of acne, prevents scarring and is an excellent skin conditioner.

For the acne cream an applicator device may be used with a cream pump.

Below, first embodiments and examples are described in relation to a use in the treatment of wound spray. However, the below embodiments and examples are not limited to only the wound application. The embodiments and examples are especially described in relation to a spray. However, the invention is not limited to this applicator device embodiment.

The wound spray is classified as a Medical Device. A medical device is a product, which is used for medical purposes in patients, in diagnosis, therapy or surgery. If applied to the body, the effect of the medical device is primarily physical, in contrast to pharmaceutical drugs, which exert a pharmacological, immunological or metabolic effect.

The composition appears to form a physical layer providing a flexible barrier with a moist environment. The algae extract and olive leaf extract in the layer create a hostile environment for bacteria. Unique aspects of the wound spray are that it has no side effects and does not influence the immune system. The product is safe, effective and is the first alternative to the traditional pharmaceutical approach using antibacterial and topical corticosteroid drugs. Bandages with hydrocolloid technology only moisturize the wound and do not have any effect on the inflamed skin, whereas the present composition does have an effect on inflammation. Effectiveness and safety of the product is proven by clinical evaluations and in vivo tests.

The vacuum spray applicator allows wide distribution of micro-droplets of the liquid formula across the injured skin surface. The Wound spray is designed as a topical medical device that forms a protective physical layer on the skin that acts as a flexible barrier protecting form unwanted external contaminants and bacterial colonization, keeping the wound protected against unfavorable effects. In addition the active ingredients in the physical layer create a hostile environment for bacteria. The formulation contains the active ingredients olive leaf extract and algae extract which inhibit bacterial growth. Furthermore the wound spray prevents scarring, is determined to relief skin irritation and treat small cuts burns and insect bites.

A good use may include the following: in case of a skin injury, clean the skin carefully and in case of a burn wound, clean the skin with lukewarm water only. Spray from a distance on the damaged and/or irritated skin (5 to 10 cm). If necessary, massage the solution on the injured skin. Apply two to three times per day or each time when necessary. Repeat treatment until the damaged and/or irritated skin is healed. If there is no improvement within seven days, we advise you to consult a health care professional. Wound spray is for external use only.

An embodiment of generating an algae extract as described may advantageously include: (1) providing the algae raw material, especially *Arthrospira platensis*; (2) one or more extractions with water; (3) combining the filtrates in case more than one extraction has been performed; (4) alcohol precipitation; (5) condensation; (6) filtration. An embodiment of generating an olive leaf extract as described may advantageously include: (1) providing the olive leaf, especially *Olea europaea* leaf; (2) extraction with solvent (ethanol+water); (3) Filtration; (4) optional concentration; (5) hydrolysis; (6) purification with organic solvent; (7) optional pasteurization for at least 2 minutes; (8) drying; and (9) optional grinding.

Analysis of an embodiment of the composition showed the presence of at least:

Polyphenols: hydroxytyrosol; tyrosol

Fatty acids: oleic acid; linoleic acid; palmitic acid; elenolic acid

Peptides: amongst others lipopetides and/or tridecapeptides (chains of 10 peptides); containing substantially all essential amino acids;

Phycocyanin (pigment protein but also antioxidant and anti-inflammatory properties);

Calcium Spirulan (sulphated polysaccharide) antiviral activity lipids

An embodiment of an algae (*Arthrospira platensis*, previously called *Spirulina Platensis* (*Arthrospira platensis*)) extract was analyzed: peptides (including lipopetide/tridecapeptide, chains of 10 peptides); Phycocyanin; Calcium Spirulan (sulphated polysaccharide) antiviral activity; lipids.

An embodiment of an olive leaf extract was analyzed: Polyphenols (hydroxytyrosol; tyrosol); Fatty acids (Oleic acid; Linoleic acid; Palmatic acid; Elenolic acid).

The invention claimed is:

1. A dermatological composition comprising:

an algae extract containing a polypeptide, and an olive leaf extract containing hydroxytyrosol, wherein the dermatological composition further comprises oleuropein originating from the olive leaf extract in a weight ratio of oleuropein to hydroxytyrosol of $<0.1$;

wherein the dermatological composition comprises the hydroxytyrosol in an amount in a range of 0.01-1 wt. % relative to the total weight of the composition;

and wherein the dermatological composition is a topical composition in a form selected from the group consisting of creams, foams, pastes, gels, lotions, ointments and emulsions.

2. The dermatological composition according to claim 1, wherein the olive leaf extract is an *Olea europaea* leaf extract and wherein the algae extract is a blue-green algae (*Arthrospira platensis*) extract.

3. The dermatological composition according to claim 1, further comprising a lipopeptide and/or tridecapeptide.

4. The dermatological composition according to claim 1, wherein the olive leaf extract is an *Olea europaea* leaf extract, obtained by extraction with a mixture of an alcohol and water and hydrolysis of the extract, and wherein the algae extract comprises an *Arthrospira platensis* extract, obtained by extraction with an aqueous liquid.

5. The dermatological composition according to claim 1, wherein the composition further comprises oleic acid, linoleic acid, palmitic acid, a lipopeptide, a tridecapeptide, phycocyanin, and lipids.

6. The dermatological composition according to claim 1, for use in the treatment and/or prevention of one or more of *P. aeruginosa, S. aureus, C. albicans, A. brasiliensis* and *E. hirae*.

7. An applicator device comprising the dermatological composition according to claim 1.

8. The applicator device according to claim 7, wherein the applicator device is a spray applicator device and wherein the dermatological composition is in an aqueous state in a container comprised by the applicator device.

9. The applicator device according to claim 7, wherein the applicator device is a pen applicator device, and wherein the dermatological composition is topical composition, such as a cream, a foam, a gel, a lotion and an ointment, powder.

10. The applicator device according to claim 7, wherein the olive leaf extract is an *Olea europaea* leaf extract and wherein the algae extract is an *Arthrospira platensis* extract.

11. A topical dressing which comprises the dermatological composition according to claim 1 impregnated therein.

12. A method for preparing the dermatological composition according to claim 1, wherein the method comprises:
 (i) treating algae with a aqueous liquid to produce an algae extract containing a polypeptide,
 (ii) treating olive leaf with an aqueous liquid comprising an alcohol to produce an olive leaf extract containing hydroxytyrosol, and
 (iii) combining the extracts and optionally combining the extracts with further compounds, to produce the dermatological composition.

13. The method according to claim 12, wherein the olive leaf comprises *Olea europaea* and wherein the algae comprises *Arthrospira platensis*.

14. A method to treat and/or prevent a dermatological microbiological infection which comprises topically applying an effective amount of the dermatological composition according to claim 1.

15. A method to treat and/or prevent a skin infection or a nail infection selected from the group consisting of nail fungus and Athlete's foot, the method comprising topically applying an effective amount of the dermatological composition according to claim 1.

16. A method to treat a wound which comprises topically applying to the wound an effective amount of the dermatological composition according to claim 1.

17. A method to treat chickenpox or acne which comprises topically applying an effective amount of the dermatological composition according to claim 1.

* * * * *